(12) United States Patent
Oggeri et al.

(10) Patent No.: US 12,402,613 B2
(45) Date of Patent: Sep. 2, 2025

(54) INSTALLATION FOR PRODUCING AND COLLECTING NEWLY-HATCHED LARVAE

(71) Applicant: Innovafeed, Nesle (FR)

(72) Inventors: Bastien Oggeri, Paris (FR); Audrey Schuller, Nogent-sur-Marne (FR); Antonin Tixier, Nanterre (FR); Antoine De Vos, Paris (FR)

(73) Assignee: Innovafeed, Nesle (FR)

( * ) Notice: Subject to any disclaimer, the term of this patent is extended or adjusted under 35 U.S.C. 154(b) by 0 days.

(21) Appl. No.: 18/560,275

(22) PCT Filed: May 9, 2022

(86) PCT No.: PCT/FR2022/050881
§ 371 (c)(1),
(2) Date: Nov. 10, 2023

(87) PCT Pub. No.: WO2022/238646
PCT Pub. Date: Nov. 17, 2022

(65) Prior Publication Data
US 2024/0237626 A1    Jul. 18, 2024

(30) Foreign Application Priority Data

May 10, 2021   (FR) ...................................... 2104933

(51) Int. Cl.
*A01K 67/36*       (2025.01)
*A01K 67/362*      (2025.01)

(52) U.S. Cl.
CPC ............ *A01K 67/36* (2025.01); *A01K 67/362* (2025.01)

(58) Field of Classification Search
CPC ....... A01K 67/36; A01K 67/362; A01K 67/34
See application file for complete search history.

(56) References Cited

U.S. PATENT DOCUMENTS

| 10,159,229 B2 * | 12/2018 | Marchant | F21V 7/22 |
| 11,985,960 B2 * | 5/2024 | van Kilsdonk | B04C 5/18 |

(Continued)

FOREIGN PATENT DOCUMENTS

| CH | 717925 A2 * | 4/2022 | A01K 67/033 |
| CN | 111887209 A * | 11/2020 | A01K 67/033 |

(Continued)

OTHER PUBLICATIONS

International Search Report for Application No. PCT/FR2022/050881 dated Aug. 19, 2022, 2 page.

(Continued)

*Primary Examiner* — Magdalena Topolski
(74) *Attorney, Agent, or Firm* — TraskBritt

(57) ABSTRACT

An installation for producing and collecting newly-hatched larvae comprises cages equipped with at least one collector of insect eggs, a transfer line for transferring the larvae from the collectors to a conveyor, and equipment for concentrating the newly-hatched larvae. It also comprises: a collection of modules grouping together a plurality of egg collectors, the modules being open at their bottom; the modules being mobile between a point of loading and the transfer line; the transfer line being open to receive the modules at the top, and at the bottom having a guide system with divergent walls, which at its top has a width tailored to the cross section of the modules and at its bottom has an opening tailored to the dimensions of a conveyor, the guide system being configured to group together the newly-hatched larvae falling from the collectors onto the upper surface of the conveyor.

15 Claims, 7 Drawing Sheets

(56) References Cited

U.S. PATENT DOCUMENTS

2020/0323173 A1   10/2020  Sabeg et al.
2023/0323173 A1   10/2023  Wang et al.

FOREIGN PATENT DOCUMENTS

| ES | 2386472 A1 * | 8/2012 | ........... A01K 67/033 |
| FR | 2460617 A1 * | 1/1981 | |
| KR | 100689671 * | 3/2007 | |
| WO | 2016/062979 A1 | 4/2016 | |
| WO | WO-2019154563 A1 * | 8/2019 | ............. A01K 29/00 |
| WO | WO-2022185480 A1 * | 9/2022 | ......... A01K 67/0339 |

OTHER PUBLICATIONS

International Written Opinion for Application No. PCT/FR2022/050881 dated Aug. 19, 2022, 7 page.

\* cited by examiner

INSTALLATION FOR PRODUCING AND COLLECTING NEWLY-HATCHED LARVAE

CROSS REFERENCE TO RELATED APPLICATIONS

This application is a national phase entry under 35 U.S.C. § 371 of International Patent Application PCT/FR2022/050881, filed May 9, 2022, designating the United States of America and published as International Patent Publication WO 2022/238646 A1 on Nov. 17, 2022, which claims the benefit under Article 8 of the Patent Cooperation Treaty to French Patent Application Serial No. FR2104933, filed May 10, 2021.

TECHNICAL FIELD

The present disclosure relates to the field of industrial farming of arthropods, in particular, of insects for the purposes of food production.

The present disclosure relates more particularly to the field of insect farming, in particular, to the black soldier fly.

BACKGROUND

Insects have a certain number of characteristics that make them well suited to use in animal feed. Insects in fact have a high protein content, while being rich in other beneficial nutrients such as fats, minerals and vitamins. The levels of protein concentration in insect meals intended for animal feed vary between 55% and 75%. The insects are characterized by a higher food conversion rate and can therefore become a very valuable feed source for farm animals. Insects are a natural component of the feed for animals such as carnivorous fish and poultry (for example, insects can provide up to 70% of the food needs of trout).

Moreover, these products also have a well-balanced nutritional profile to meet human food needs.

These considerations have led to the development of the large-series automated production of food from arthropod farming, and more particularly insects, in industrial sites organized into complementary spaces specialized in the hatching, rearing and collection of mature animals and the processing thereof to extract the compounds of interest.

These industrial sites must be optimized to allow the industrialization of large volumes of larvae. One of the critical steps relates to the collection of the eggs laid by the female insects and the concentration of larvae for breeding thereof because they are very small, fragile living beings that are initially highly dispersed, and that must be grouped together as homogeneously as possible by batches of newly-hatched larvae all having the same maturity stage in a given batch. For the purposes of this patent, "newly-hatched larvae" will be understood to mean young larvae originating from freshly hatched eggs. Generally, laying is carried out in cages confining the flies in an enclosed space wherein collectors having laying surfaces, for example, grooved plates, are arranged, on which the females deposit the eggs. These collectors are recovered to then allow the hatching of eggs giving rise to newly-hatched larvae that are gathered in containers, at stages that are as homogeneous as possible, before being distributed on an insect-raising medium in insect-raising modules. The step that is the subject matter of this patent relates to the hatching of eggs and the grouping of the newly-hatched larvae.

The present disclosure relates to a system allowing the hatching of eggs, previously collected on collectors, and then the transport and the assay of the newly-hatched larvae obtained following the hatching of the eggs, before their inoculation in an insect-raising medium to allow their growth.

Different solutions for industrial collection and grouping in a container of newly-hatched larvae, especially insects, are known in the art.

International patent application WO2019154563A1 describes a method for rearing and collecting young larvae, in particular, black soldier flies, comprising placing insects in a cage, comprising egg depositing means, guiding larvae, having been hatched from the deposited eggs, by means of a guiding device, placed under the cage, under the influence of gravity toward a conveyor belt placed under the guiding means, moving the larvae by means of the conveyor belt to a container placed at the end of the conveyor belt, counting the number of larvae on the conveyor belt before collection in the container, and collecting the larvae from the conveyor belt in the container until a predetermined number of larvae has been reached.

Document FR2460617 describes an installation for the mass production of eggs from an insect, in particular, of the meal moth type, of the type comprising an incubator containing cell elements, a hatcher and a nest-box, characterized by the fact that the incubator consists of a ventilated enclosure comprising moving supports for stacks of cell elements arranged along their horizontal plane, a hatcher intended to contain moving supports for stacking the elements in parallel and on edge in line with an outlet hopper and provided with an inlet for carbon dioxide, and a nest-box comprising an arrangement of sheets in parallel and arranged on edge in line with an outlet hopper toward a collector member, the hatcher, the nest-box and the collector being connected in succession by a pneumatic transport duct, the incubator, the hatcher and the nest-box further being provided with components for regulating temperature and, optionally, ventilation.

BRIEF SUMMARY

The present disclosure aims to overcome the disadvantages of the solutions known in the prior art by proposing a novel solution suitable for large-scale industrial mass production, while limiting production losses.

To this end, the present disclosure relates, according to its most general acceptance, to an installation for producing and collecting newly-hatched larvae, comprising a collection of cages equipped with at least one collector of eggs laid by the insects present in the cages, a line for transferring the larvae newly hatched from the hatched eggs from each of the collectors to a conveyor, and equipment for concentrating the newly-hatched larvae coming from the conveyor in order to convey them to an insect-raising module or to a newly-hatched-larvae buffer storage container, characterized in that the installation further comprises:
 a collection of modules grouping together a plurality of egg collectors, the modules being open at the bottom;
 the modules being mobile between a point of loading with the collectors removed from the cages and the newly-hatched-larvae transfer line;
 the newly-hatched-larvae transfer line being open, with no casing at the top, in order to receive the modules at the top, and at the bottom having a guide system with divergent walls, referred to as a receptacle, which at its top has a width tailored to the width of the modules and at its bottom has an opening tailored to the dimensions of a conveyor, the receptacle being configured to group together the newly-hatched larvae falling under the effect of gravity from the collectors onto the upper surface of the conveyor.

Advantageously, the conveyor comprises at least one moving band, positioned under the lower opening of the receptacle with divergent walls.

According to one variant, the conveyor comprises a vibrating chute positioned under the lower opening of the receptacle with divergent walls.

According to one variant, the receptacle with divergent walls is constituted by a slotted gutter having two lateral blanks whose lower edges are separated by a longitudinal slot.

Advantageously, the receptacle with divergent walls comprises, in the upper part, means for longitudinal movement of the modules.

According to a particular embodiment, the transfer line comprises, in the upper part of the receptacle with divergent walls, means for moving the modules parallel to the moving band.

Advantageously, the moving band has a horizontal main section extended at its downstream end by a section inclined toward a suction system, a vibrating means acting on the upper section and/or on the lower section.

Preferably, the moving band has a horizontal main section extended at its downstream end by a section inclined toward a suction system, the lower band of this section being subjected to an air flow directed in the direction opposite the passage of the lower band.

According to a particular embodiment, the installation comprises a pneumatic transport system by suction for conveying newly-hatched larvae from the conveyor to a means for distributing the newly-hatched larvae.

According to a preferred variant, the installation comprises a cyclone separator formed by a cylinder and/or a vertical cone wherein an upward air flow is produced, and the bottom of which comprises a mechanical and periodic discharge means.

Advantageously, the mechanical and periodic discharge means consists of a lock with rotary blades.

Preferably, the installation also comprises a means for metering the quantity of newly-hatched larvae by weighing.

Preferably, the installation comprises a routing system for distributing the collected newly-hatched larvae onto the trays of a multi-stage module.

The present disclosure also relates to a method for raising and collecting the newly-hatched larvae of arthropods, comprising the following steps:

a) having a collection of cages filled with insects, provided with at least one egg collector enabling the female insects to deposit their eggs;

b) collecting the newly-hatched larvae under the influence of gravity toward a conveyor ensuring the movement of the newly-hatched larvae through the conveyor to a collection means;

characterized in that a grouping step is carried out for grouping a plurality of collectors in modules as well as a step of moving the modules onto an open transfer line comprising a slotted gutter having two convergent walls defining a slot for pouring the newly-hatched larvae onto a conveyor toward the downstream end for harvesting the newly-hatched larvae.

Advantageously, introducing a new module on the transfer line advances the modules already positioned in the installation in the downstream direction.

The present disclosure also relates to a module for attaching egg collectors, characterized in that it consists of an open armature formed by a rigid assembly, whereupon transverse roller rails are provided between which frames can be inserted each supporting a plurality of collectors for eggs from the laying cages.

BRIEF DESCRIPTION OF THE DRAWINGS

The present disclosure will be better understood on reading the following description, with reference to the appended drawings showing non-limiting embodiments, in which.

DETAILED DESCRIPTION

Figure 1:
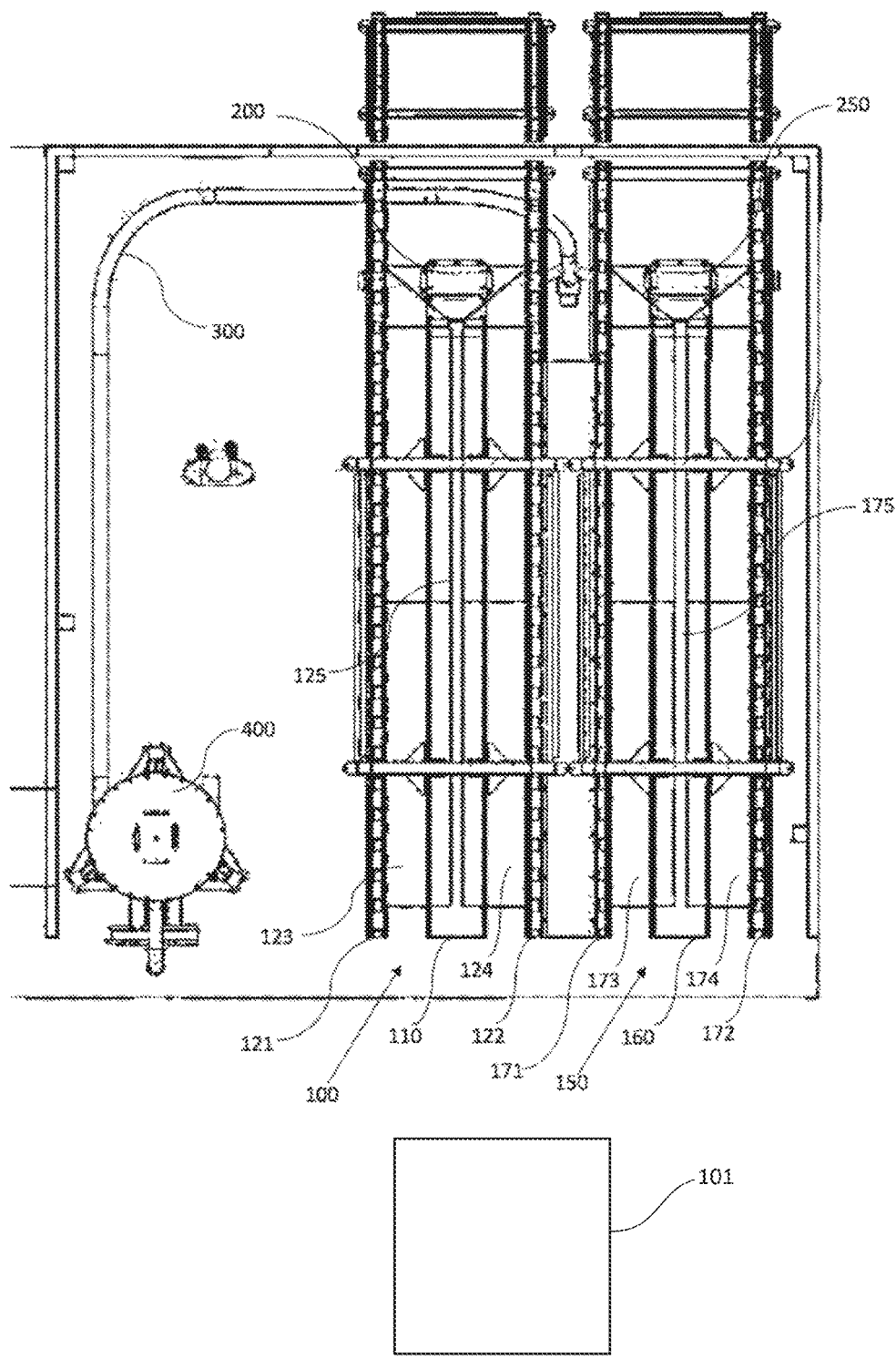
FIG. 1 shows a schematic top overview of an installation for producing and collecting newly-hatched larvae according to the present disclosure.

In the following description, some details are developed with reference to equipment, and in a passage. This does not preclude the same details from also being present in the equipment mentioned in another passage, even in a passage concerning another alternative embodiment, simply because the details in question have not been subject to a new description.

In the present patent, the term "comprising," used in the claims, should not be interpreted as being limited to the elements or steps listed hereinafter; it does not exclude other elements or steps. It should be interpreted as specifying the presence of the features, steps or components mentioned, but does not exclude the presence or addition of one or more other features, steps or components, or groups thereof. Thus, the scope of the expression "a device comprising A and B" should not be limited to devices consisting only of components A and B, but as regards the present disclosure, the only listed components of the device are A and B, and additionally, the assertion must be interpreted as including equivalents of these components.

General Principles

The industrial production of food from arthropod farming and—in the example described in a non-limiting manner—of insects is done in large, automated facilities intended to create the optimal conditions for massively allowing the passage of the evolution stage of the egg, from the egg pod or newly-hatched larva to the adult insect, passing through the larva (or maggots or apterans) and the nymph or pupa.

Typically, these installations are organized into several buildings comprising shelving for storing the insect-raising modules loaded with an insect-raising medium inoculated with larvae under climate conditions favorable to rearing, and handling equipment for episodic treatments.

The present disclosure aims to improve the yield of the zone from the hatching of the eggs to inoculation of the newly-hatched larvae in their insect-raising medium. To do this, the first issue is to have the best possible hatching rate, that is, most eggs hatch and become newly-hatched larvae.

Then, the second issue is to ensure effective transport of the newly-hatched larvae to their growth container, without them being able to escape from the system.

Finally, the last issue is to ensure precise quantification of newly-hatched larvae of the same age in order to limit the variability in the process. Indeed, this step is essential for the rest of the insect-raising cycle. If there are too many newly-hatched larvae relative to the amount of insect-raising medium, then their growth will not be optimal because they will not have enough food. Conversely, if there are not enough newly-hatched larvae, the insect-raising medium will not be completely consumed, which will pose problems for the downstream steps of the cycle, in particular, for the step of separating the larvae and their insect-raising medium. Likewise, if the newly-hatched larvae have different ages, it will be difficult to properly control their growth.

Another cross-cutting issue is having reliable, robust, inexpensive technologies and the lowest possible consumption of consumables such as, for example, compressed air.

Collection Process

The collection process is included between the laying process, which is carried out upstream of the collection in laying cages, and the rearing process, which takes place downstream of the collection, in modules filled with insect-raising medium.

Figure 2:
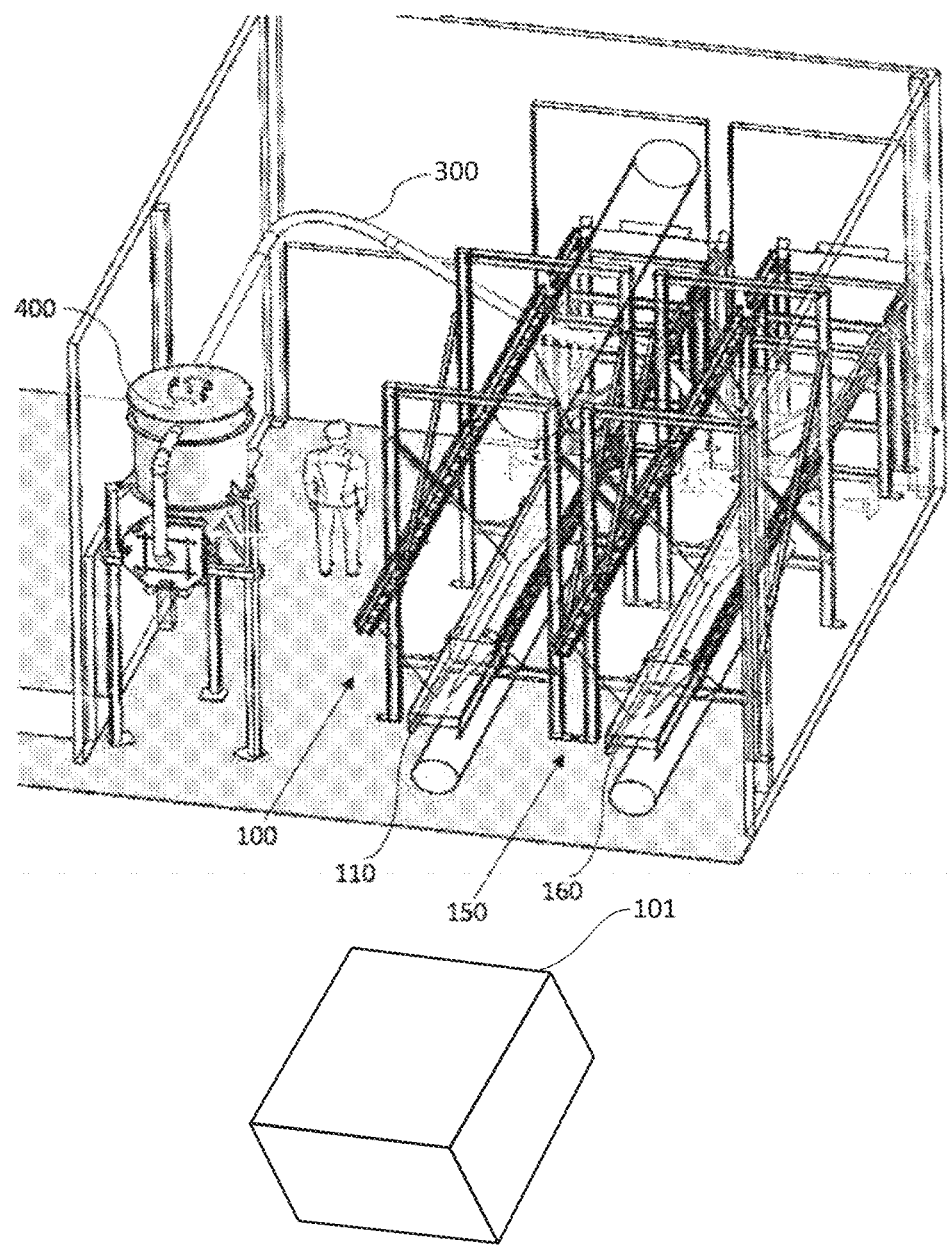
FIG. 2 shows a schematic perspective view of an installation for producing and collecting newly-hatched larvae according to the present disclosure.

The steps of the collection process are carried out in one and the same zone, for example, a building or a hangar, wherein equipment items shown by FIGS. 1 and 2 are located. In this zone there is a climate-controlled environment favorable to egg hatching, except for the inoculation part, which is carried out in a different zone.

Figure 3:
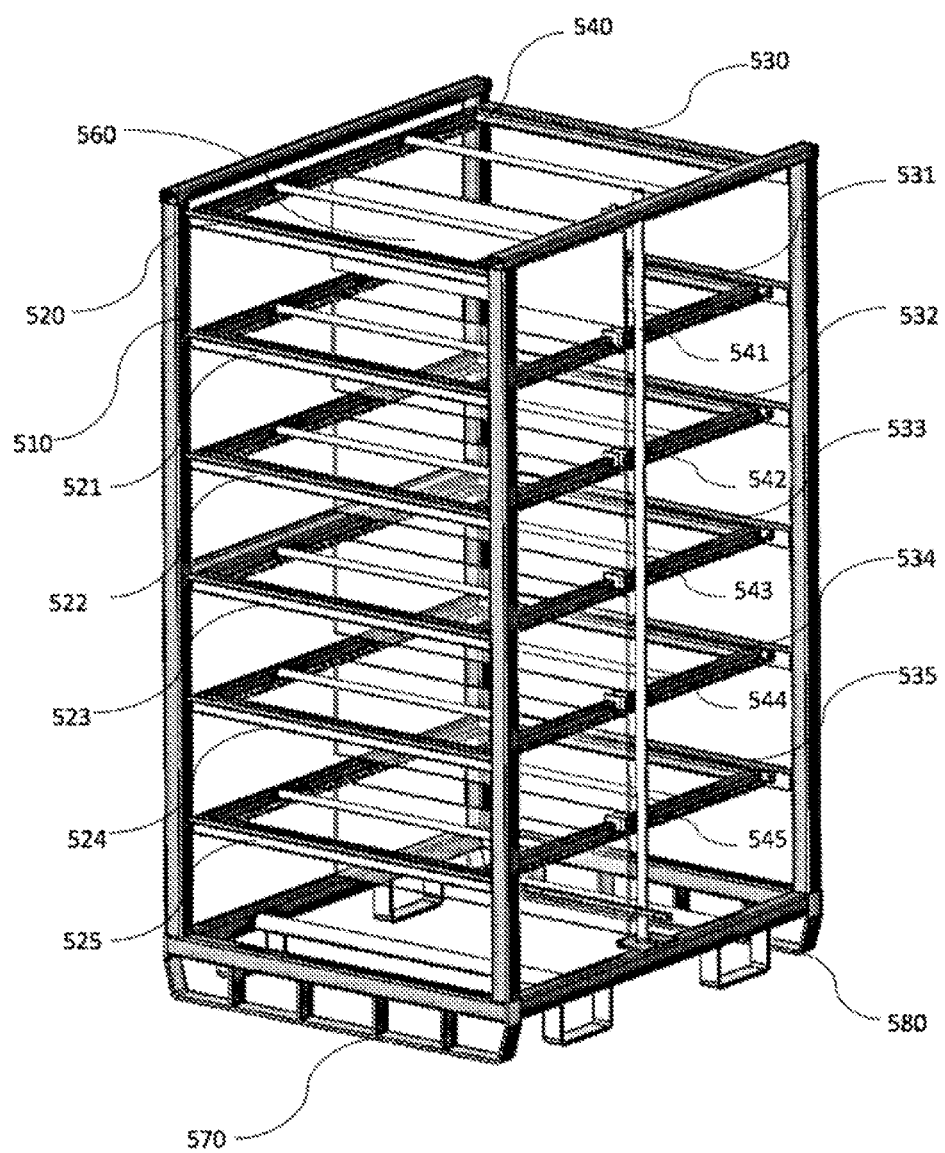
FIG. 3 shows a perspective view of a module for receiving laying collectors.
Figure 8:
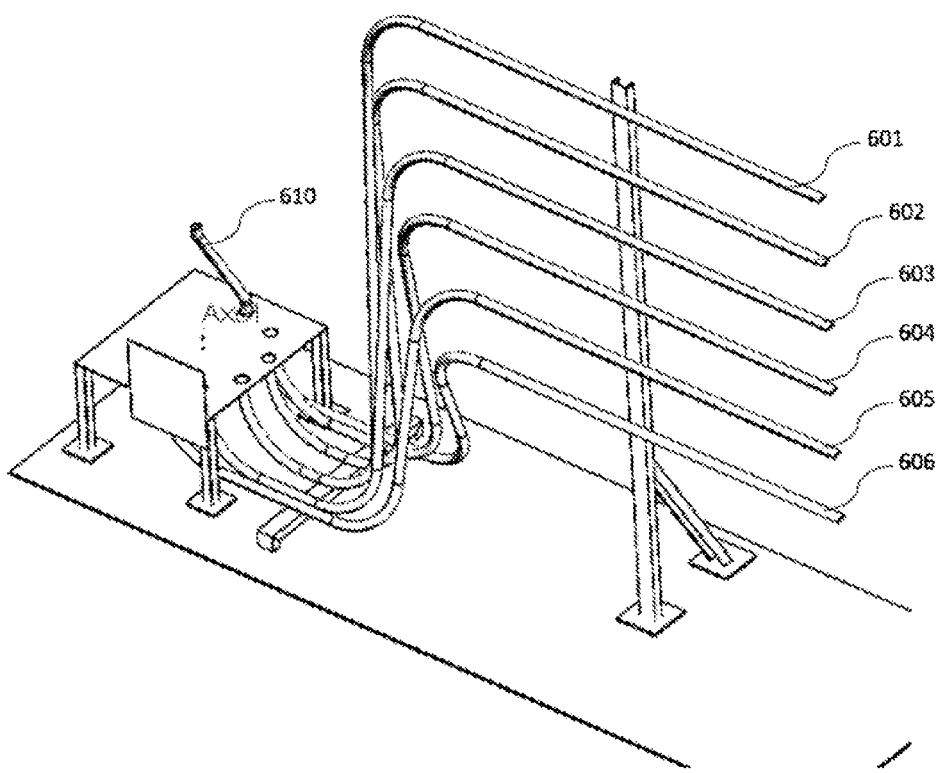
FIG. 8 shows a perspective view of the routing system.

The equipment used for these steps mainly comprises:
a plurality of modules shown in FIG. 3, intended to receive the collectors extracted from the cages;
newly-hatched-larvae transfer line (100, 150) comprising roller bearing rails (121, 122; 171, 172) intended for longitudinal movement of the aforementioned collector modules (500, 501), and the moving bands (110, 160);
a suction system (300) for transferring to a cyclone separator (400); and
a distribution system for supplying the insect-raising module with newly-hatched larvae, shown in FIG. 8.

The eggs arrive in the hatching zone on collectors coming from another zone wherein the flies have previously laid eggs on the collectors, generally in a cage. These collectors are, for example, in the form of grooved plates. They are arranged on modules having roller rails for receiving collectors designed specifically to allow a high density of eggs (and therefore then of newly-hatched larvae), without creating interference during the gravity drop of the newly-hatched larvae, while being configured for easy handling by standard handling machines.

The system for supporting and transporting these collector modules on the transfer lines (100, 150) leaves the appropriate time for all the eggs to hatch. To do this, the collector modules are moved using a passive mechanical transport according to a first in, first out (FIFO) logic (the last collector module to arrive expels the oldest from the zone).

Once they have hatched, the newly-hatched larvae fall by gravity onto the moving bands (110, 160). During their fall, the newly-hatched larvae fall into a slotted gutter and are guided by lateral blanks (123, 124; 173, 174) forming inclined planes opening onto longitudinal slits (125, 175) located in line with the moving bands (110, 160). Since the newly-hatched larvae are sticky, it is important to choose the material of the surface of the gutters to limit the adhesion of the newly-hatched larvae to this surface as much as possible. Typically, these slotted gutters are made by forming mirror polished stainless steel sheets, that is, with a roughness less than 0.2 microns.

The newly-hatched larvae are then recovered at the end of the moving bands (110, 160), but without being stored at this location. Since the newly-hatched larvae are "sticky," a specific configuration to detach them at the end of the moving bands (200, 250) is provided and is described in more detail below.

To further increase the production, the transfer lines and associated equipment may be replicated as many times as necessary and operate in parallel.

At the end of the moving bands, the automation chain is not broken. The newly-hatched larvae are then transported pneumatically to a cyclone separator (400). The latter can work indifferently under overpressure or under depression. A simple mechanical system allows periodic opening and closing of this cyclone separator (400) in order to convey the newly-hatched larvae to the next step.

After the cyclone separator (400) and after its periodic opening and closing system, for example, a lock with rotary blades, a buffer zone is necessary. It thus makes it possible to be able to store the quantity of newly-hatched larvae necessary in order to produce continuously and to be able to ensure a continuous supply of newly-hatched larvae for the downstream phases of the process.

The various elements of the installation are described below by way of example, in more detail. These various elements can be combined together or combined with other elements fulfilling the same function to form an installation according to the present disclosure.

Detail of the Egg Collector

The collectors have a rectangular shape with dimensions 850 mm×230 mm. Their two faces are grooved. It is in these grooves that the female flies lay eggs during the prior laying step. After the flies have laid eggs, the collectors are recovered, for example, by a handling operator, and are grouped together on collector modules (500, 501) of collectors.

Detail of the Module

A module is made up of an open parallelepipedal armature (510) formed by an assembly of rigid welded tubes, whereupon slides are provided, for example, formed by transverse roller rails (520 to 525, 530 to 535) between which frames (540 to 545) can be inserted each supporting a plurality of collectors (560) for eggs from the laying cage.

These collector modules (500, 501) can support up to 240 collectors. The overall shape of the collector modules is parallelepipedal with dimensions of 1200 mm×1000 mm×1800 mm; the structure is provided by an outer chassis, thus allowing all the space necessary in the center for the newly-hatched larvae to be able to drop by gravity once the eggs have hatched. The collectors are suspended from profiles passing through the chassis of the collector rack owing to screws. The armature rests on pads (570, 580).

The bases of the modules have a very particular shape in order to easily allow them to be handled by conventional transporters, but also to be able to be compatible with the use of a roller conveyor.

The collector (560) modules (500, 501) are stored in the climate-controlled environment on roller bearing rails (121, 122; 171, 172).

A module is loaded with frames (540 to 545) whereupon a series of egg collectors (560) freshly removed from the laying cage have been attached, simultaneously (to within the handling time) so that all the collectors contain eggs of the same maturity, the difference in maturity being dependent on the rate of collection of the collectors. This time generally does not exceed a few hours.

Figure 4:
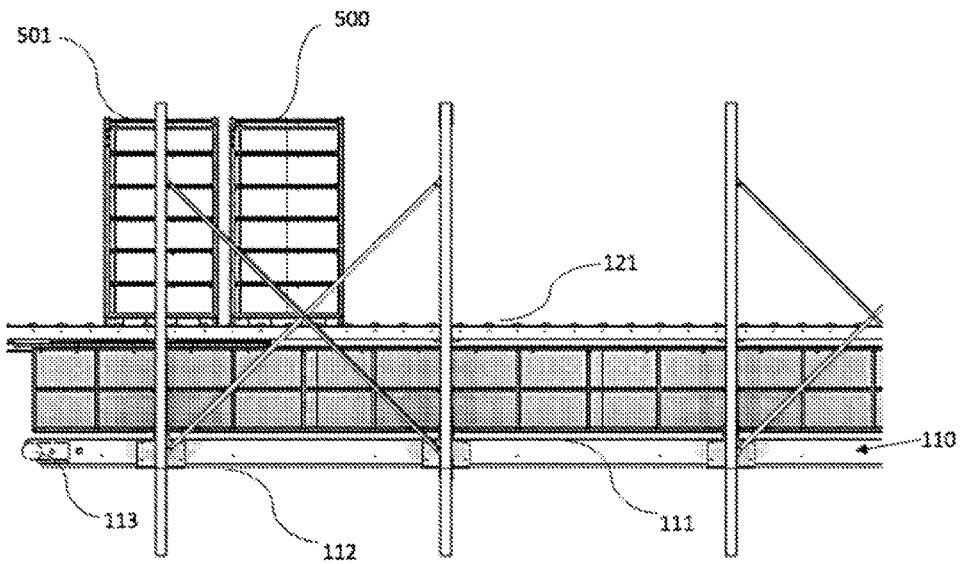
FIG. 4 shows a side view of two modules and a transfer line.
Figure 5:
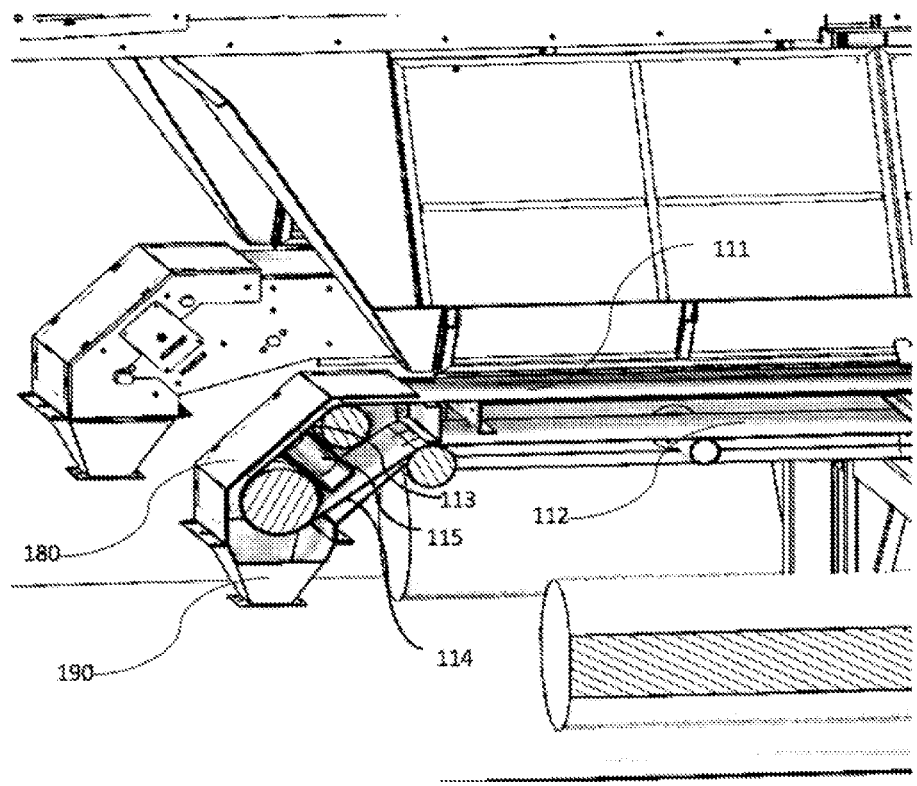
FIG. 5 shows a perspective view of the downstream end of the moving band.
Figure 6:
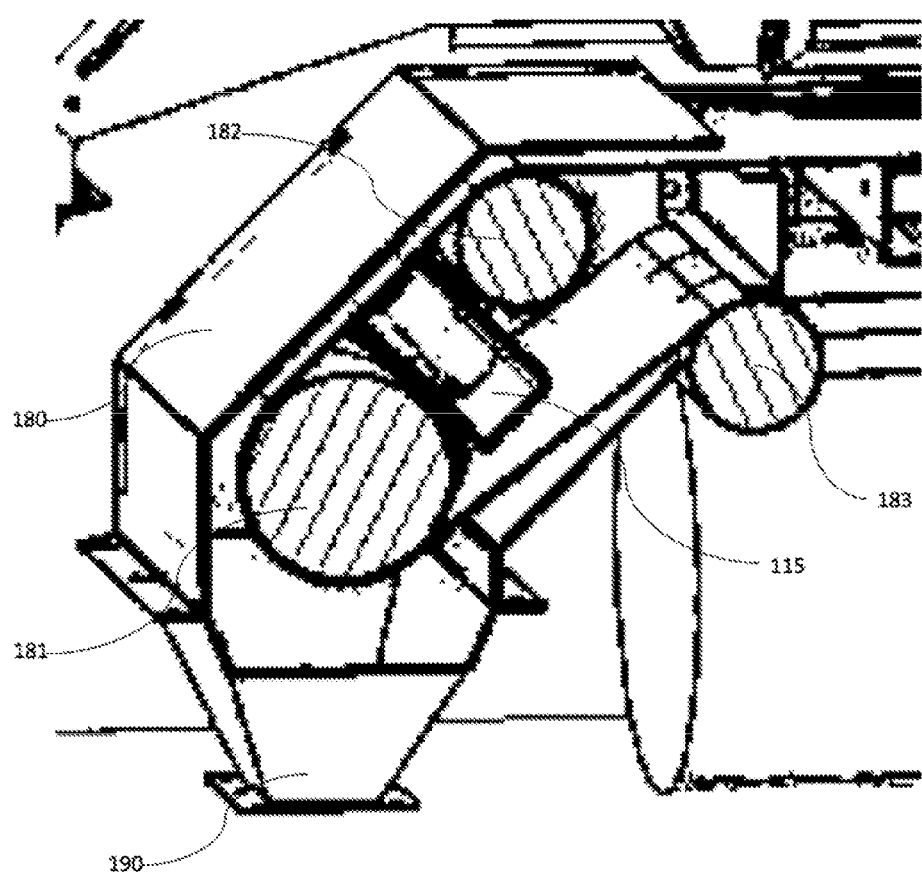
FIG. 6 shows an enlarged perspective view of the downstream end of the moving band.

Once loaded, it is moved to the transfer line (100, 150) and deposited on the roller bearing rails (121, 122; 171, 172). In the example shown in FIG. 4, the introduction of a new module pushes the collector module(s) (500) already placed on the transfer line in the downstream direction. It is possible to move the collector modules (500, 501) manually, by pushing back the series of modules already placed on the roller bearing rails (121, 122; 171, 172) using the last collector module (501), which causes the assembly to advance, and the oldest module is recovered at the downstream end of the transfer lines (100, 150) to then be returned to the area where the laying cages are located in order to be reloaded with new egg collectors (560).

The moving band (110) forms a loop with an upper segment (111) arranged under the slot opening between the two inclined blanks, and a lower segment (112) for the return of the band that passes through an upstream roller (113).

During the residence of a module on the transfer line, the newly-hatched larvae naturally fall when the eggs hatch and are grouped together, owing to the slotted gutter, onto the surface of the moving band (110, 160), which advances at a speed allowing the larvae laid on its surface to be concentrated so as to bring them to a suction system provided at the downstream end of the conveyor.

Detail of the Upstream Part of the Transfer Line

The transfer line consists of a rack supporting roller bearing rails (121, 122; 171, 172) for moving the collector modules (500, 501) above a slotted gutter returning the newly-hatched larvae that fall from the collectors (560) onto the surface of a moving band. The rack comprises a motorized mechanism ensuring the driving of this band by means of drive rollers.

The newly-hatched larvae must not stick excessively to the moving band at the risk of being too difficult to detach. Conversely, they must adhere a small amount so as not to fall off the sides of the band and to be well transported. A quite suitable material is non-adhesive polyurethane.

The working length of the moving bands (110, 160) is 15 m to correspond to the length of the roller conveyor located above, which in turn is determined by the residence time and the number of modules to ensure the intended production.

The width of the moving bands is 400 mm: a band that is too narrow would promote the escape of newly-hatched larvae at the sides, and an overly wide band would make it more difficult to manage detaching them at the end of the band.

The band moves at a nominal speed of 0.1 m/s in the same direction as the direction of movement of the modules. The majority of the eggs hatch at the end of their residence in the zone; the newly-hatched larvae will thus mainly fall at the end of the moving bands.

The storage of these collector modules (500, 501) is done according to FIFO (First In First Out). The last collector module (500, 501) arriving on the roller conveyor pushes the one that has been in the zone the longest toward the outside of the zone. The movement of the modules is therefore a passive mechanical movement.

On average, the modules spend 4 days in the zone. This time is determined so that all of the eggs have time to hatch and the newly-hatched larvae fall by gravity onto the moving band located under the roller conveyor.

The roller conveyor has 15 module locations.

In order to guide the falls of newly-hatched larvae, planes inclined by 55° have been installed.

Detail of the Downstream Part of the Transfer Line

The moving band (110, 160) of the transfer line ends with a segment having an upper part (113) and a sloped return part (114), with an inclination of 45° over a length of 260 mm protected from the air currents by a sheet forming a canopy (180).

This slope has a double advantage:
it increases the residence time of the newly-hatched larvae in the zone where they must be detached, which therefore considerably increases the separation ratio;
the newly-hatched larvae that are already detached slide on the band and take newly-hatched larvae located downstream with them, and optionally those that were not yet detached.

This modification of the orientation of the moving band is carried out by a system of rollers (181, 182, 183).

A first striker (115) is installed at the end of the moving band, in its inclined part, in order to vibrate the upper segment (111) of the band and to aid the separation of the newly-hatched larvae. This is, for example, an electromagnetic vibrator vibrating at a frequency of a few tens of Hertz and with an amplitude of a few millimeters.

For better efficiency, a second striker is added just after, in the zone between the first striker and the reversing roller (181). In this zone, the tension of the band is the highest, which allows more effective vibrations to promote separation.

An aeraulic system produces a counter-current jet of air, relative to the direction of travel of the return part (114) of the inclined segment in order to detach any newly-hatched larvae that may remain stuck. The stronger the blowing, the more effective the separation function will be. Conversely, the blowing must remain limited so as not to create an excessive air flow on the forward face of the moving band and risk creating fly-offs and therefore loss of newly-hatched larvae on the forward face of the moving band. A scraper or brush system can also be added in order to detach the newly-hatched larvae.

At the downstream end of the moving band, the assembly is turned over as close as possible. Since the newly-hatched larvae are very light, the slightest parasitic air flow can disrupt the system; it is therefore important to turn over the assembly, to promote preferential air flows and to avoid stray air flows.

Finally, at the end of the moving bands, a junction mouth (190) ensures the turning over of the system in order to allow the passage of the newly-hatched larvae by pneumatic transport to a cyclone separator (400), at an air speed of between 5 and 10 m/s. This junction part has a funnel shape in order to avoid retentions.

In this example of the present disclosure, this assembly consisting of the roller conveyor, the gutter, inclined planes and the moving band is installed twice in parallel to have doubled production. The newly-hatched larvae coming from these two parallel assemblies are, however, transported pneumatically to the same cyclone separator (400).

Suction System

The cyclone separator (400) is formed by a vertical double-walled cylinder, of diameter 950 mm. This cyclone separator (400) allows a limited ascensional speed of 0.25 m/s. This speed must be low to prevent the newly-hatched larvae from rising.

This cyclone separator terminates in a lock with rotary blades. The latter part turns continuously, alternating phases where the newly-hatched larvae are poured and phases where the newly-hatched larvae are blocked in the cyclone separator. The specific design of the lock is such that this mechanical separation does not damage or crush the newly-hatched larvae. This lock is made of stainless steel to prevent adhesion. To avoid the crushing of the newly-hatched larvae, this lock has 6 blades, which is the minimum number making it possible to ensure good sealing. It rotates at a reduced speed of 6 rpm.

Metering System and Vibrating Chute on Weight Indicator

After this cyclone separator, a metering step is necessary in order to have the desired quantity of newly-hatched larvae so that the downstream part of the process is carried out optimally. Here, the choice was made to quantify the amount of newly-hatched larvae by weighing, unlike the prior art, which uses optical counting. Weighing has the double advantage of being easy to implement and being sufficiently precise relative to the need. Furthermore, given the quantities of newly-hatched larvae targeted for the present disclosure, optical counting may prove to be limiting, either due to the image processing time, or if the stream of newly-hatched larvae is uninterrupted on the scrolling band.

Figure 7:
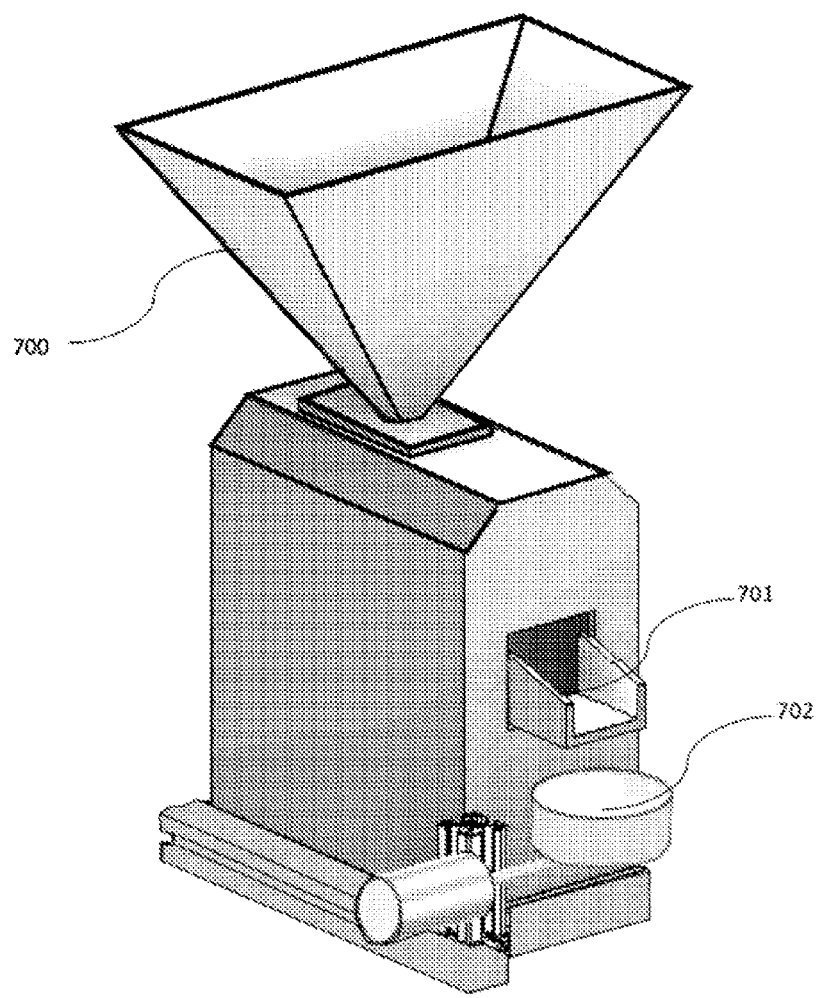
FIG. 7 shows a perspective view of the distribution hopper of the larvae.

The weighing unit shown in FIG. 7 comprises a hopper (700) in the upper part in the form of a funnel for collecting the newly-hatched larvae coming from the cyclone separator (400). These newly-hatched larvae fall into the vibrating chute (701). By vibration, this chute (701) pours the newly-hatched larvae little by little into the turning bucket (702) until the desired mass of newly-hatched larvae is reached in this bucket.

The volume of this funnel-shaped hopper (700), serving as a buffer zone, is defined to guarantee good production fluidity. The vibrating chute (701) is actuated by a vibration system in order to avoid clogging and to help the newly-hatched larvae to flow.

As soon as one of the trays of a multi-stage module is ready to be inoculated, the turning bucket (702) is tilted into a funnel and the newly-hatched larvae are transported pneumatically toward this tray via a routing system.

The benefit of this turning bucket (702) is to be able to directly begin weighing the next dose while the inoculation is in progress. This thus makes it possible to parallelize the operations and therefore to have a better timing of the production.

Routing System

This routing system shown in FIG. 8 allows the larvae to be inoculated in the assembly of six trays of a multi-stage module, without this module requiring movement. This inoculation is carried out sequentially, each tray being inoculated one after the other.

The distribution device comprises 6 ramps (601 to 606) regularly spaced apart with a pitch corresponding to the interval of the trays of a multi-stage insect-raising module. The length of these ramps is determined based on the dimensions of the trays in order to allow the distribution of the newly-hatched larvae on the surface of the insect-raising medium lining the tray.

The operation of this 6-way routing system is based on the movement of the mobile chute (610) located directly downstream of the funnel. This mobile chute (610) changes position to connect to one of the ramps (601 to 606) constituting the feeder chutes of each tray one after the other. A dose can be done every 26 seconds; only 156 seconds are necessary to fully inoculate a multi-stage module.

"Intermittent" Operation

The assembly of elements described above operates according to an intermittent sequence. Indeed, since the newly-hatched larvae fall gradually over the moving bands, it is not necessary to rotate it continuously. However, it is also not possible to stop it for a prolonged period to prevent newly-hatched larvae from escaping by the sides. The optimal intermittent sequence was defined empirically by an operating period of 8 minutes, then a stop of 5 minutes, and so on.

The main benefit of this intermittent operation is to achieve energy savings and to reduce consumption (in particular, of compressed air) without having the slightest impact on production, in particular, owing to the buffer storage.

The invention claimed is:

1. A rearing installation for producing and collecting newly-hatched larvae, comprising a collection of cages equipped with at least one collector of eggs laid by insects in the cages, and a transfer line for transferring the newly-hatched larvae newly hatched from the eggs from each of the collectors to a conveyor, a collection of modules grouping together a plurality of egg collectors, the modules being open at bottoms of the modules;
    wherein the modules are mobile between a point of loading with the collectors removed from the cages and the transfer line; and
    wherein the transfer line is open, with no casing at a top of the transfer line, in order to receive the modules at the top, and at a bottom, the transfer line has a guide system receptacle with divergent walls configured to group the larvae under gravity while minimizing lateral dispersion, which at its top has a width tailored to a cross section of the modules and at its bottom has an opening tailored to the dimensions of a conveyor, the receptacle being configured to group together the newly-hatched larvae falling under the effect of gravity from the collectors onto the upper surface of the conveyor.

2. The installation for producing and collecting newly-hatched larvae of claim 1, wherein the conveyor comprises at least one moving band positioned under the opening at the bottom of the receptacle with divergent walls.

3. The installation for producing and collecting newly-hatched larvae of claim 2, wherein the installation further comprises a suction system, the at least one moving band has a horizontal main section extended at its downstream end by a section inclined toward the suction system, and a vibrating means is configured to act on an upper section of the at least one at least one moving band and/or on a lower section of the at least one moving band.

4. The installation for producing and collecting newly-hatched larvae of claim 2, wherein the at least one moving band has a horizontal main section extended at its downstream end by an inclined section, a lower band of the inclined section being subjected to an air flow directed in a direction opposite a passage direction of the lower band.

5. The installation for producing and collecting newly-hatched larvae of claim 1, wherein the conveyor comprises at least one portion with vibrating means positioned at an end of the conveyor.

6. The installation for producing and collecting newly-hatched larvae of claim 1, wherein the receptacle with divergent walls comprises a slotted gutter having two lateral blanks, lower edges of the two lateral blanks being separated by a longitudinal slot.

7. The installation for producing and collecting newly-hatched larvae of claim 6, wherein the receptacle with divergent walls comprises, in an upper part of the receptacle, means for longitudinal movement of the modules.

8. The installation for producing and collecting newly-hatched larvae of claim 1, further comprising a pneumatic transport system for conveying the newly-hatched larvae from the conveyor to a means for distributing the newly-hatched larvae.

9. The installation for producing and collecting newly-hatched larvae of claim 1, further comprising a cyclone separator formed by a cylinder and/or a vertical cone wherein an upward air flow is produced, and a bottom of which comprises a mechanical and periodic discharge device.

10. The installation for producing and collecting newly-hatched larvae of claim 1, further comprising a metering device for metering a quantity of newly-hatched larvae by weight.

11. The installation for producing and collecting newly-hatched larvae of claim 1, further comprising a routing system for distributing the newly-hatched larvae collected on trays of a multi-stage module.

12. The installation for producing and collecting newly-hatched larvae of claim 1, the modules of the collection of modules comprising an open armature formed by a rigid assembly, whereupon transverse roller rails are provided, the transverse roller rails configured to receive frames supporting the plurality of egg collectors.

13. A method for raising and collecting newly-hatched larvae of arthropods, comprising:

providing a collection of cages filled with insects, provided with at least one egg collector enabling female insects to deposit their eggs; and collecting the newly-hatched larvae under the influence of gravity toward a conveyor ensuring movement of the newly-hatched larvae along the conveyor to a collection means;

wherein a plurality of collectors are grouped in modules, and the modules are moved onto an open transfer line comprising a slotted gutter having two convergent walls defining a slot for pouring the newly-hatched larvae onto the conveyor toward a downstream end for harvesting the newly-hatched larvae.

14. The method for raising and collecting the newly-hatched larvae of arthropods of claim 13, wherein introduction of a new module on the transfer line advances modules already positioned on the transfer line in a downstream direction.

15. A rearing installation for producing and collecting newly-hatched larvae, comprising a collection of cages equipped with at least one collector of eggs laid by insects in the cages, and a transfer line for transferring the newly-hatched larvae newly hatched from the eggs from each of the collectors to a conveyor, a collection of modules grouping together a plurality of egg collectors, the modules being open at bottoms of the modules;

wherein the modules are mobile between a point of loading with the collectors removed from the cages and the transfer line;

wherein the transfer line is open, with no casing at a top of the transfer line, in order to receive the modules at the top, and at a bottom, the transfer line has a guide system receptacle with divergent walls configured to group the larvae under gravity while minimizing lateral dispersion, which at its top has a width tailored to a cross section of the modules and at its bottom has an opening tailored to the dimensions of a conveyor, the receptacle being configured to group together the newly-hatched larvae falling under the effect of gravity from the collectors onto the upper surface of the conveyor;

wherein the conveyor comprises at least one moving band positioned under the opening at the bottom of the receptacle with divergent walls; and wherein the at least one moving band has a horizontal main section extended at its downstream end by an inclined section, a lower band of the inclined section being subjected to an air flow directed in a direction opposite a passage direction of the lower band.

* * * * *